US008313893B2

(12) United States Patent
Wee et al.

(10) Patent No.: US 8,313,893 B2
(45) Date of Patent: Nov. 20, 2012

(54) METHOD OF DECELLULARIZING PORCINE CORNEA

(75) Inventors: Won-Ryang Wee, Seoul (KR); Mee-Kum Kim, Gyeonggi-Do (KR); Joo-Youn Oh, Seoul (KR)

(73) Assignee: SNU R&DB Foundation, Seoul (KR)

( * ) Notice: Subject to any disclaimer, the term of this patent is extended or adjusted under 35 U.S.C. 154(b) by 359 days.

(21) Appl. No.: 12/596,087

(22) Filed: Oct. 15, 2009

(65) Prior Publication Data

US 2011/0183404 A1  Jul. 28, 2011

Related U.S. Application Data

(63) Continuation of application No. PCT/KR2009/001770, filed on Apr. 6, 2009.

(30) Foreign Application Priority Data

Mar. 4, 2009 (KR) .................. 10-2009-0018294

(51) Int. Cl.
*A01N 1/00* (2006.01)
*A61F 2/14* (2006.01)
(52) U.S. Cl. ....................................... 435/1.1; 623/5.11
(58) Field of Classification Search .................. None
See application file for complete search history.

(56) References Cited

U.S. PATENT DOCUMENTS

2005/0256588 A1* 11/2005 Sawa et al. .................. 623/23.72
2009/0202977 A1*  8/2009 Ott et al. ........................ 435/1.2

OTHER PUBLICATIONS

Marquez et al., "Decellularization of bovine corneas for tissue engineering applications", Acta Biomaterialia 5 :1839-1847 (Feb. 2009).*
Lin et al., "Lamellar keratoplasty with a graft of lyophilized acellular porcine corneal stroma in the rabbit", Veterinary Ophthalmology 11 (2) : 61-66 (2008).*
Xu et al., "Development of a rabbit corneal equivalent using an acellular corneal matrix of a porcine substrate" Molecular Vision 14 : 2180-2189 (2008).*
Joo Youn Oh, et al.; "Lamellar corneal pig-to-rabbit xenotransplantation", Letter to the Editor, Xenotransplantation, p. 198-199, 2008.
Joo Youn Oh, et al.; "Histological differences in full-thickness vs. lamellar corneal pig-to-rabbit xenotransplantation", Veterinary Opthamology, p. 78-82, 2009.

* cited by examiner

*Primary Examiner* — Sandra Saucier
(74) *Attorney, Agent, or Firm* — Edwards Wildman Palmer LLP; Kongsik Kim; Elbert Chiang

(57) ABSTRACT

Disclosed is a method for processing porcine cornea using an aqueous NaCl solution and an aqueous trypsin/EDTA solution to decellularize enucleated porcine cornea. The porcine cornea processed by the method causes neither inflammation nor immune rejection. The porcine corneal stroma decellularized by the method can be recellularized together with host keratocytes after transplantation.

11 Claims, 10 Drawing Sheets

METHOD OF DECELLULARIZING PORCINE CORNEA

CROSS-REFERENCES TO RELATED APPLICATIONS

This application is a continuation of PCT/KR2009/001770 filed on Apr. 6, 2009 which claims priority to Korean Application No. 10-2009-0018294 filed on Mar. 4, 2009. The entire contents of the aforementioned patent applications are incorporated herein by this reference.

BACKGROUND

1. Technical Field

The present invention relates to a method for processing porcine cornea, and more particularly to a method for processing porcine cornea for decellularization.

2. Related Art

The cornea is an organ refracting light, which accounts for one-sixth of the outermost tunic of the eyeball. The cornea is comprised of a total of five layers, i.e., corneal epithelium, Bowman's membrane, corneal stroma (also substantia propria), Descemet's membrane and corneal endothelium. The corneal epithelium consists of five to six layers of cells. The basal cells of the corneal epithelium arise from stem cells at the limbus, migrate towards the centre of the cornea and are exfoliated in seven days. The Bowman's membrane is composed of acellular collagen fibers and is colorless and transparent. However, the Bowman's membrane cannot be regenerated, scarring normally occurs upon surgical operation or traumatic injury. The corneal stroma makes up approximately 90% of the thickness of the cornea and has uniformly arranged cells with a uniform size. Descemet's membrane consists of three to four layers of cells and is considered to be the base membrane for the corneal endothelial cells. The corneal endothelium is a monolayer of cells, is composed of specialized endothelial cells, is extremely restricted in terms of regeneration, and its cell number decreases with age. When the number of cells decreases, the cells increase in size to fill the void.

Meanwhile, corneal blindness, which results from loss of corneal transparency, is a major cause of vision loss, second only to cataracts. Ocular trauma and corneal ulceration annually blind 1.5 to 2 million individuals. The only efficient treatment for such blindness is transplantation of human donor corneas (also called "keratopasty"). A shortage of donor corneas has brought about the need for an alternative to allograft.

A great deal of research has been conducted into corneal replacements. Synthetic replacement materials include keratoprostheses and natural corneal materials which are tissue-engineered using cultured cells and extracellular matrix (ECM).

However, at present, these materials are not commonly used due to problems associated with biocompatibility and optical and mechanical properties, and xenograft utilizing other animal corneas instead of human corneas is the fastest growing method.

Porcine corneas are the most promising replacement for human corneas, because they have a refractive index and size comparable to human corneas, the use of porcine for transplantation is regarded as ethically acceptable and genetically-modified pigs (e.g., α-1,3-galactosyltransferase knockout pigs and hDAF transgenic pigs) have been developed and are finally entering into clinical practice.

However, conventional research reports that corneal full-thickness xenografts induce severe immune rejection. In addition, research reported by the present inventors showed that lamellar corneal xenografts in the absence of the corneal endothelium still encountered immune rejection [Oh, J. Y., Kim, M. K., Wee, W. R. *Lamellar corneal pig-to-rabbit xenotransplantation. Xenotransplantation* 15, 198, 2008; Oh, J. Y., Kim, Ko, J. H., Lee, H. J., Park, C. G., Kim, S. J., Wee, W. R., Lee, J. H. *Histological differences in full-thickness versus lamellar corneal pig-to-rabbit xenotransplantation. Vet Ophthalmol* 12, 78, 2009]. This means that keratocytes (corneal stromal cells) may also cause immune rejection.

Accordingly, the inventors of the present invention considered that acellular porcine corneal stroma (that has been deprived of cells) may be useful as a donor tissue for lamellar corneal xenograft in patients who have normal endothelial cells but suffer from stromal opacities. Furthermore, the recent paradigm of corneal transplantation has changed from full-thickness corneal grafting, in which the overall area is replaced, to partial-thickness corneal grafting, in which only the diseased area is replaced. Such access is regarded as more useful for clinical practice.

A great deal of acellular biological materials is used to repair defects in various organs and various decellularization methods are researched.

However, in-depth research has not been conducted on methods for decellularizing corneal stroma, and in particular, research has not been made on methods for efficiently processing corneas, while minimizing immune responses and pathogenicity after transplantation and maintaining corneal transparency.

The above information disclosed in this Background section is only for enhancement of understanding of the background of the invention and therefore it may contain information that does not form the prior art that is already known in this country to a person of ordinary skill in the art.

SUMMARY

Therefore, the present invention has been made in view of the above problems, and it is an object of the present invention to provide a method for efficiently processing corneas, while minimizing immune response and pathogenicity after keratoplasty and maintaining corneal transparency.

In accordance with the present invention, the above and other objects can be accomplished by the provision of a method for processing porcine cornea, including: immersing enucleated porcine cornea in an aqueous NaCl solution; immersing the porcine cornea in an aqueous trypsin/EDTA solution; and washing the porcine cornea.

The use of the aqueous NaCl solution and the aqueous trypsin/EDTA solution enables reduction of immune response and inflammation and aids decellularization.

The aqueous NaCl solution may contain 1.0 to 2.0 M NaCl.

The step of immersing the porcine cornea in an aqueous NaCl solution may be carried out at a temperature of 35 to 39° C. for 12 to 36 hours.

The aqueous trypsin/EDTA solution may contain 0.01 to 0.10% (w/v) trypsin and 0.01 to 0.05% (w/v) EDTA.

The step of immersing the porcine cornea in an aqueous trypsin/EDTA solution may be carried out at a temperature of 35 to 39° C. for 36 to 60 hours.

The washing may be carried out using phosphate buffered solution (PBS) as a washing solution.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
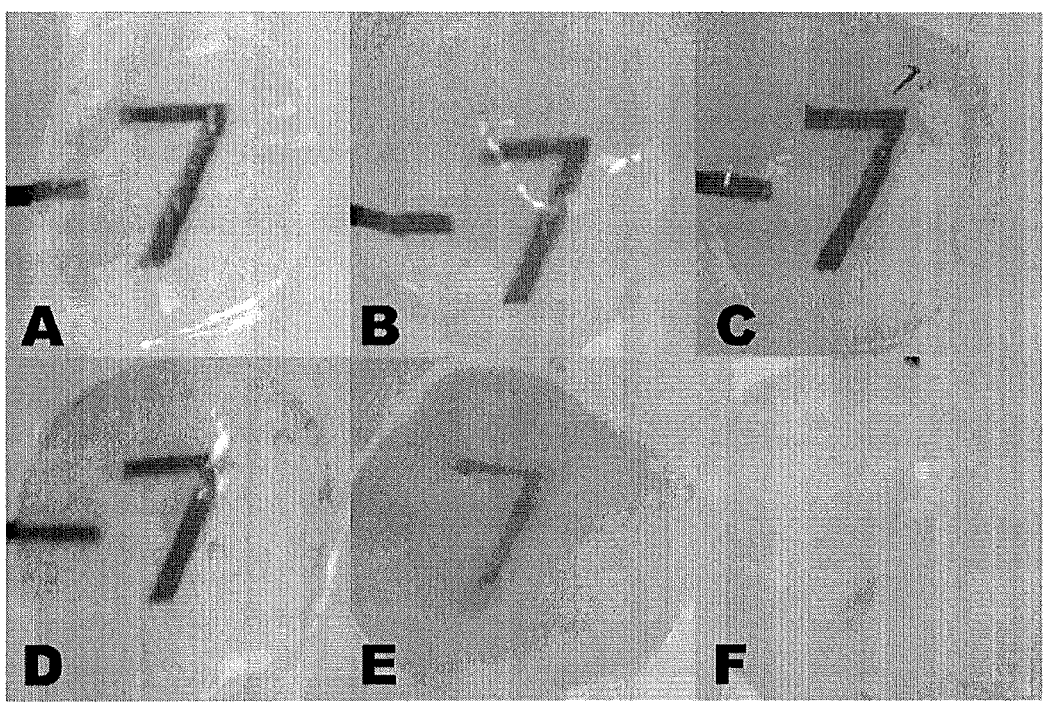
FIG. 1 is images of porcine cornea for a non-treated control group (A), 3-times freezing-thawing group (B), hypertonic saline group (C), hyperosmolar glycerol group (D), trypsin/Dispase/SDS group (E) and DNase/RNase group (F). The corneas of the 3-times freezing-thawing group, hypertonic saline group and hyperosmolar glycerol group maintained optical transparency, but the corneas in the trypsin/Dispase/SDS group and DNase/RNase group lost optical transparency.

Hereinafter, the present invention will be illustrated in detail below.

Optimal corneal replacements for lamellar graft or overlay graft must exhibit mechanical and optical properties similar to human corneas, induce no immune response, be nontoxic to neighboring ocular tissues and have functionally active extracellular matrices.

The two reasons for the importance of the corneal extracellular matrix are as follows.

First, the extracellular matrix acts as a biological scaffold providing optimal micro-environments required for corneal recovery and regeneration.

Second, the extracellular matrix, which is made of collagen, accounting for 70% or more of corneal dry weight, has a lamellar morphology of thin collagen fibers, thus being indispensable to corneal transparency.

Thus, in spite of strenuous efforts to develop corneal replacements, clinically applicable replacements have yet to be obtained.

Meanwhile, the present inventors considered that porcine corneas have the potentiality of extracellular matrices of human corneas, because they have similar physical and refractive properties thereto. In accordance with previous research of the present inventors, porcine corneas show rejection responses four weeks post-operation, in spite of anterior lamella grafting [Oh, J. Y., Kim, M. K., Wee, W. R. *Lamellar corneal pig-to-rabbit xenotransplantation. Xenotransplantation* 15, 198, 2008; Oh, J. Y., Kim, M. K., Ko, J. H., Lee, H. J., Park, C. G., Kim, S. J., Wee, W. R., Lee, J. H. *Histological differences in full-thickness versus lamellar corneal pig-to-rabbit xenotransplantation. Vet Ophthalmol* 12, 78, 2009.].

Accordingly, the present inventors determined to reduce immune responses from porcine corneas by destroying cells via physical (freezing, repetition of freezing-melting process), chemical (hypertonic, hyperosmolar) or enzymatic treatments. The reason is that collagen has low antigenicity, while cells have high antigenicity [Dufrane, D., Cornu, O., Delloye, C., Schneider, Y. J. *Physical and chemical processing for a human dura mater substitute. Biomaterials* 23, 2979, 2002; Minami, A., Usui, M., Ishii, S., Kobayashi, H. *The in*

*vivo effects of various immunoreactive treatments on allogeneic tendon grafts. J Hand Surg [Am]* 8, 888, 19, 1983].

As a result of tests according to the present invention, an experimental group, "1.5 mol NaCl, 0.05% trypsin and 0.02% EDTA" reduces immune responses, most efficiently preserves the collagen structure, is suitably incorporated into host corneas and maintains corneal transparency without causing inflammation or rejection responses for six months after partial-grafting into rabbits.

Meanwhile, one Comparative Experimental group, i.e., the "freezing-group" did not sufficiently remove cells from porcine corneas and underwent rejection responses at the same time as the control group, i.e., fresh porcine corneas.

Also, another Comparative Experimental group, i.e., "three-times freezing-melting group" induces rejection responses two months post-graft due to cell remainders left after treatment.

Also, another Comparative Experimental group, "hyperosmolar glycerol group" or "trypsin/Dispase/SDS group" induces severe apoptosis to obtain dead cell fragments, triggering immune responses of the rabbit eyeball, and undergoes early rejection responses.

Also, other Comparative Experimental groups, "trypsin/Dispase/SDS group" and "Dnase/Rnase group" severely destroy collagen structures, causing removal and segmentation of all collagen fibers of porcine corneas. In addition, the treated porcine corneas lost transparency and were fused.

Meanwhile, the notable issue of the present invention is that decellularized porcine corneal stroma of the Comparative Experimental group, i.e., hypertonic saline group, was recellularized together with host corneal stemal cells after transplantation. The total corneal thickness and graft thickness of the hypertonic saline group increased, like the contralateral non-grafted eye. This indicates that keratocytes reproliferated in the porcine cornea stroma are functionally active and produce extracellular matrices. The recellularization of decellularized grafts is important, because keratocytes play an essential part in maintenance and metabolism of corneal stroma [McLaughlin, C. R., Fagerholm, P., Muzakare, L., Lagali, N., Forrester, J. V., Kuffova, L, Rafat, M. A., Liu, Y., Shinozaki, N., Vascotto, S. G., Munger, R., Griffith, M. *Regeneration of corneal cells and nerves in an implanted collagen corneal substitute. Cornea* 27, 580, 2008; Salvalaio, G., Fasolo, A., Bruni, A., Frigo, A. C., Favaro, E., Ponzin, D. *Improved preparation and preservation of human keratoplasty lenticules. Ophthalmic Res* 35, 313, 2003; Muller, L. J., Pels, E., Vrensen, G. F. J. M. *The effects of organ-culture on the density of keratocytes and collagen fibers in human corneas. Cornea* 20, 80, 2004].

Hereinafter, examples will be provided for a further understanding of the invention. The following examples are for illustrative purposes only and are not intended to limit the scope of the present invention.

EXAMPLES AND COMPARATIVE EXAMPLES

Sample Preparation for Examples of the Present Invention (Experimental Groups) and Comparative Examples (Comparative Experimental Groups)

Porcine corneas were obtained from brother-sister mated miniature adult pigs (12-month old) immediately after death. The epithelium was treated with ethanol and then peeled off. Then, the cornea was treated with phosphate buffered solution (PBS) and an antibiotic three times every 30 minutes with stirring. A 250 μm-thick anterior lamella was obtained from the porcine cornea using an 8.0 mm-diameter Trephine (Kai industries Cp. Ltd, Seki city, Tokyo).

The cornea was divided into seven groups, as set forth in TABLE 1 below and was treated in accordance with the following procedure. Each group included five eyes (n=5)

(1) Non-treated fresh cornea (Control group), (2) cornea frozen at −20° C. for one week and then thawed at room temperature (Freezing group), (3) Cornea obtained by freezing in a 50 ml-tube containing liquid nitrogen for 15 minutes, rapidly thawing at 37° C. and repeating the freezing-thawing process three times (3-times freezing-thawing group), (4) Cornea obtained by immersion in a 1.5 M NaCl solution, maintaining at 37° C. for 24 hours, in a 0.05% trypsin/0.02% EDTA aqueous solution (ethylenediaminetetraacetic acid, Sigma Aldrich) at 37° C. for 48 hours, and washing with PBS three times (Hypertonic saline group), (5) cornea obtained by storing in a 98% glycerol solution at 4° C. for 21 days, washing with PBS, maintaining in a 0.05% trypsin/0.02% EDTA solution at 37° C. for 48 hours, and washing with PBS three times (Hyperosmolar glycerol group), (6) cornea obtained by immersing in 0.25% trypsin solution at 4° C. for 24 hours, in a 0.1% sodium dodecyl sulfate (SDS) solution at room temperature for 6 hours, treating with 560 unit/1 dispase solution at 4° C. for 12 hours, treating with a 0.1% SDS solution at room temperature for 6 hours, and washing with PBS three times (Trypsin/Dispase/SDS group), (7) cornea obtained by immersing in a 0.1 M NaOH solution at 25° C. for 2 hours, treating with 40 U/mL Dnase and RNase with stirring and thoroughly washing with PBS (Dnase/RNase group).

The corneas were stored at 4° C., before being used for each group.

TABLE 1

| Groups | | Treatment method |
|---|---|---|
| Control group | Non-treated group | Non-treated fresh cornea |
| Freezing group | Comparative Example (Comparative experimental group) | Frozen at −20° C. for one week and then thawed at room temperature |
| 3-times freezing-thawing group | Comparative Example (Comparative experimental group) | Freezing in a 50 ml-tube containing liquid nitrogen for 15 minutes, rapidly thawing at 37° C. and repeating the freezing-thawing process three times |
| Hypertonic saline group | Example (Experimental group) | Storing in a 98% glycerol solution at 4° C. for 21 days, washing with PBS, maintaining in a 0.05% trypsin/0.02% EDTA solution at 37° C. for 48 hours, and washing with PBS three times |
| Hyperosmolar glycerol group | Comparative Example (Comparative experimental group) | Immersing in 0.25% trypsin solution at 4° C. for 24 hours, in a 0.1% sodium dodecyl sulfate (SDS) solution at room temperature for 6 hours, treating with 560 unit/1 dispase solution at 4° C. for 12 hours, treating with a 0.1% SDS solution at room temperature for 6 hours, and washing with PBS three times |
| Trypsin/Dispase/SDS group | Comparative Example (Comparative experimental group) | Immersing in 0.25% trypsin solution at 4° C. for 24 hours, in a 0.1% sodium dodecyl sulfate (SDS) solution at room temperature for 6 hours, treating with 560 unit/1 dispase solution at 4° C. for 12 |

TABLE 1-continued

| Groups | | Treatment method |
| --- | --- | --- |
| | | hours, treating with a 0.1% SDS solution at room temperature for 6 hours, and washing with PBS three times |
| Dnase/RNase group | Comparative Example (Comparative experimental group) | Immersing in a 0.1M NaOH solution at 25° C. for 2 hours, treating with 40 U/mL Dnase and RNase with stirring and thoroughly washing with PBS |

Experimental Example 1

Ex Vivo Evaluation of the Corneal Stroma Decellularized in Accordance with the Method Set Forth in Table 1 Above 1. Macroscopic Analysis Macro-analysis revealed that the corneas for the control group, freezing group, 3-times freezing-thawing group, hypertonic saline-treated group, and hyperosmolar glycerol-treated group remained transparent, whereas the corneas for trypsin/Dispase/SDS-treated group and DNase/RNase-treated group became opaque (FIG. 1).

2. Microscopic Analysis

First, the porcine cornea for each group was sectioned and stained with a hematoxylin and eosin (H&E) staining method. Then, the H&E-stained slices were observed under an optical microscope (Olympus Optical Co. Ltd., Tokyo, Japan).

Figure 2:
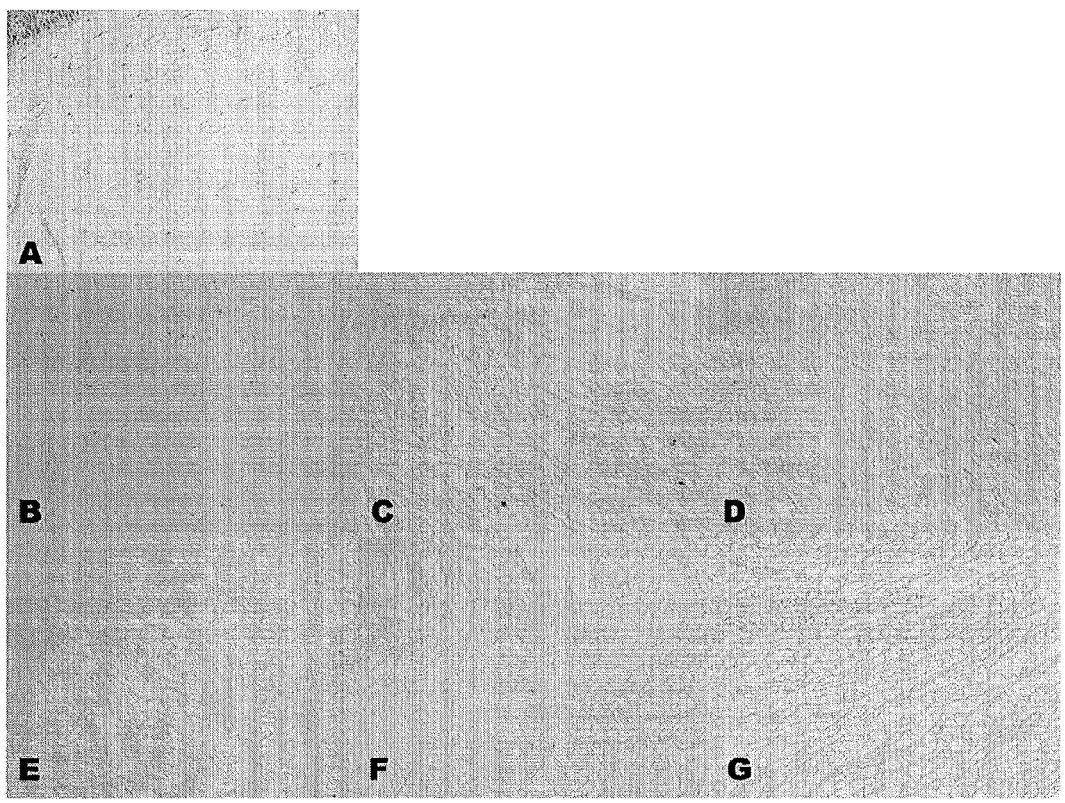
FIG. 2 shows hematoxylin-eosin stained porcine corneas from control group (A), 3-times freezing-thawing group (B), hypertonic saline group (C), hyperosmolar glycerol group (D), trypsin/Dispase/SDS group (E), and DNase/RNase group (F). The 3-times freezing-thawing group, hypertonic saline group, hyperosmolar glycerol group and trypsin/Dispase/SDS group have almost no cells, but the DNase/RNase group had severely-deformed collagens without any cellular structure.

The H&E-stained 3-times freezing-thawing group, hypertonic saline group, hyperosmolar glycerol group and trypsin/dispase/SDS group had almost no cells. On the other hand, the control group and the freezing group had many nuclei throughout the corneal stroma (FIG. 2). The Dnase/Rnase group had no cell and underwent severe deformation in collagen structure, which was the reason behind the corneal opacity observed during macroscopic analysis.

Meanwhile, the decellularization mechanism of the porcine cornea was analyzed with TUNEL assay using ApopTag® Plus Fluorescein in situ apoptosis detection kit (Chemicon international, Billerica, Mass., USA). The apoptotic cells were observed with a fluorescent microscope (BX 61, Olympus, Shinjuku, Tokyo, Japan).

Figure 3:
FIG. 3 shows TUNEL assay results of porcine corneas for control group (A), freezing group (B), 3-times freezing-thawing group (C), hypertonic saline group (D), hyperosmolar glycerol group (E), trypsin/Dispase/SDS group (F) and DNase/RNase group (G). The control group and freezing group had no apoptotic cells. On the other hand, the hyperosmolar glycerol group and trypsin/Dispase/SDS group had many apoptotic cells.

As a result of TUNEL assay, the hyperosmolar glycerol group and trypsin/Dispase/SDS group had quite a few positively-stained nuclei, the 3-times freezing-thawing group partially had positively-stained nuclei, and the hypertonic saline group had almost no nuclei (FIG. 3).

As a result of the TUNEL assay, the nuclei for the control group and the freezing group were not positively stained. This is the reason that the groups did not undergo apotosis.

Meanwhile, the reason for no-staining of the Dnase/Rnase group by H&E and TUNEL staining is that Dnase and Rnase were treated in absence of cellular or nuclear fragments.

Meanwhile, to evaluate delicate injury to the corneal cells and collagens, the corneas were fixed in 2.5% glutaraldehyde PBS (pH 7.2), maintained at 4° C. overnight, and fixed in osmium tetroxide for one hour. The sample was washed again, and dehydrated with serial dilution in ethanol. The sample was mounted on a stub, sputter-coated with gold and then observed via TEM (JEM-1400 JEOL, Tokyo, Japan).

Figure 4:
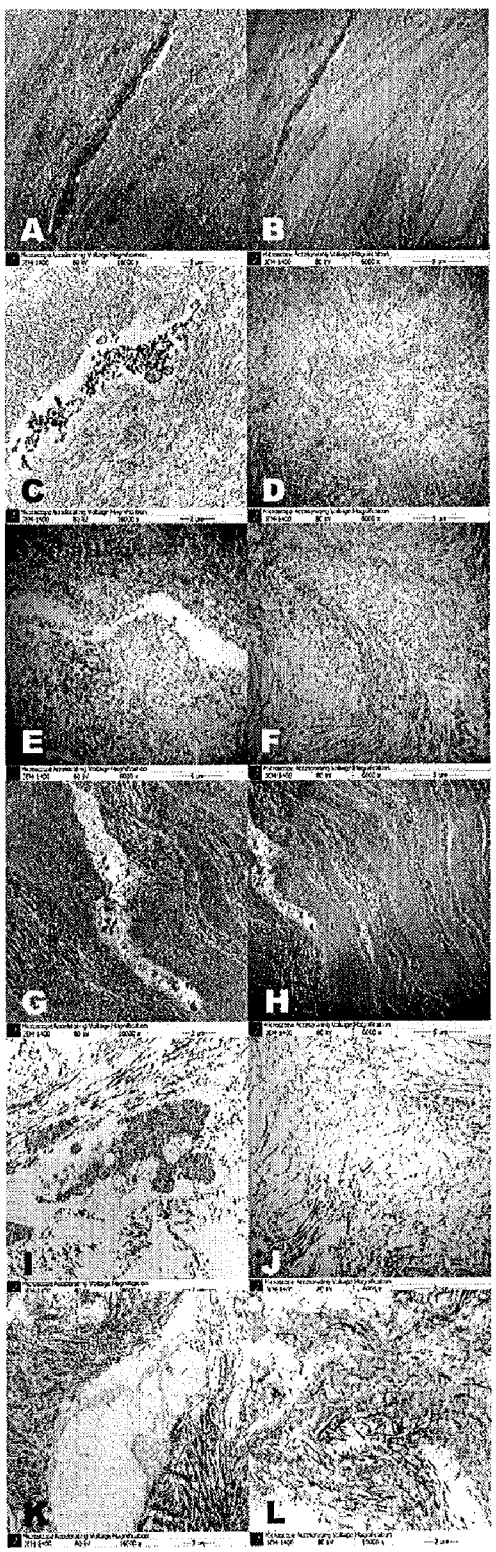
FIG. 4 is transmission electron microscope (TEM) images of porcine corneas of control group (A, B), 3-times freezing-thawing group (C, D), hypertonic saline group (E, F), hyperosmolar glycerol group (G, H), trypsin/Dispase/SDS group (I, J), and DNase/RNase group (K, L). The control group had normal keratocytes between well-structured collagen bundles. On the other hand, the corneas of other groups had severely-damaged cells. The trypsin/Dispase/SDS group and DNase/RNase group had excessively-fragmented collagen fibers with no cellular structures.

From the TEM findings, it can be seen that the control group, the fresh cornea, had normal keratocytes between well-structured collagen lamellae. However, the 3-times freezing-thawing group and the hyperosmolar glycerol group suffered notable cellular damage by apoptotic keratocyte remnants (FIG. 4). In particular, the cornea of the hypertonic saline group had no visible cells or remnants thereof, but had normally preserved and arranged collagen bundles. On the other hand, the corneas of the trypsin/Dispase/SDA group and the Dnase/RNase group had only hollows without cellular structure due to severely-destroyed cytoplasm. In addition, for these two groups, collagen fibers were disappeared or severely fragmented, indicating breakage of the collagen lamellae morphology.

3. Evaluation of Keratocyte Viability

In order to evaluate keratocyte viability, the corneas were fragmented and incubated in a medium for keratocyte culture (DMEM/F-12, 10% FBS, and 1% penicillin-streptomycin (Lonza, Basel, Switzerland).

Figure 5:
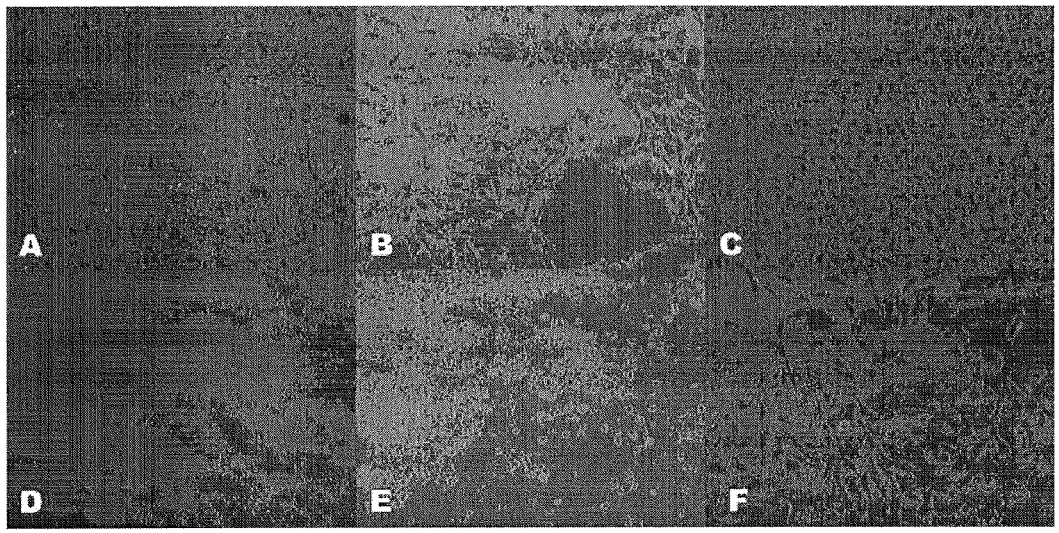
FIG. 5 shows morphologies of porcine keratocytes (A, B, C) cultured from normal corneas and porcine keratocytes (D, E, F) cultured from corneas frozen and thawed three times. As compared to the normal corneas, the 3-times frozen-thawed porcine corneas had grown fewer cells 1 week (A, D), 2 weeks (B, E) and three weeks (C, F) post-operation.

The keratocytes of the 3-times freezing-thawing group were grown very slowly, as compared to those of the control group (FIG. 5). However, the keratocytes of the hypertonic saline group, the hyperosmolar glycerol group, trypsin/Dispase/SDA group and the Dnase/Rnase group did not grow, in spite of being cultured for 21 days.

Experimental Example 2

Identification of In Vivo Efficiency of Decellularized Corneal Stroma on Xenograft Model 1. Evaluation for Clinical Course of Corneal Xenograft A 2-3 kg adult New Zealand white rabbit (Orient Bio Inc., Seoungnam, Korea) was used as a recipient animal for keratoplasty in the present experimental Example 2. The rabbit was anesthetized by intramuscularly administering 10 mg/kg zolazepam (Zoletil®, Yuhan Corp., Seoul, Korea) and 6.8 mg/kg xylazine hydrochloride (Rompun®, Bayer, Frankfurt, Germany).

For graft of porcine corneas, a 250 μm-thick anterior lamellar graft of the porcine cornea was marked with an 8.0 mm-diameter trephine and manually detached with a crescent knife (Alcon Surgical, Fort Worth, Tex., USA). The anterior lamellar grafts of the porcine cornea (N=7 for each group) were sutured with eight stitches into the recipient cornea of the rabbit by interrupted suture using a 10-0 nylon suture (Ethicon, Somerville, N.J., USA). At one week, all sutures were removed. Full-thickness eyelid suturing was performed and maintained for one week. A levofloxacin antibiotic eye drop (Cravit®, Santen Pharmaceutical Co., Ltd., Osaka, Japan) was administered to the operated rabbit twice daily and a whole body antibiotic (Gentamicin®, 40 mg/kg body weight; Abbott Laboratories, North Chicago, Ill., USA) was intramuscularly administered thereto.

The grafted cornea was observed three times monthly with a slit lamp microscope. Herein, the rejection response was defined to the condition in which a graft completely lost transparency (i.e., the condition wherein corneal periphery and iris structures are entirely shielded by the graft).

As a result of the observation, the corneas of the control group, freezing group, 3-times freezing-thawing group, hypertonic saline group and hyperosmolar glycerol group were suitably incorporated into the grafted rabbit corneas and completely re-epithelialized by the host epithelium after one week. The porcine corneal stroma of the control group and the freezing group was transparent until 2 weeks post-graft into the rabbit.

However, the corneas became opaque and all of grafted corneas were completely opaque during 4 weeks post-grafting. The grafts of the 3-times freezing-thawing group were transparent for one month, but showed rejection response two months post-operation. The porcine corneas of the hypertonic saline group all maintained optical transparency, without rejection response or inflammation for 6 months post-grafting.

Meanwhile, at 3 weeks post-operation, the porcine cornea-grafted rabbit eyes for the hyperosmolar glycerol group underwent inflammation and neovascularization and were then fully opacified.

Meanwhile, porcine corneal lamellae of the trypsin/Dispase/SDA group and the Dnase/Rnase group were fused just after transplantation into rabbits and the grafts lost transparency.

Figure 6:
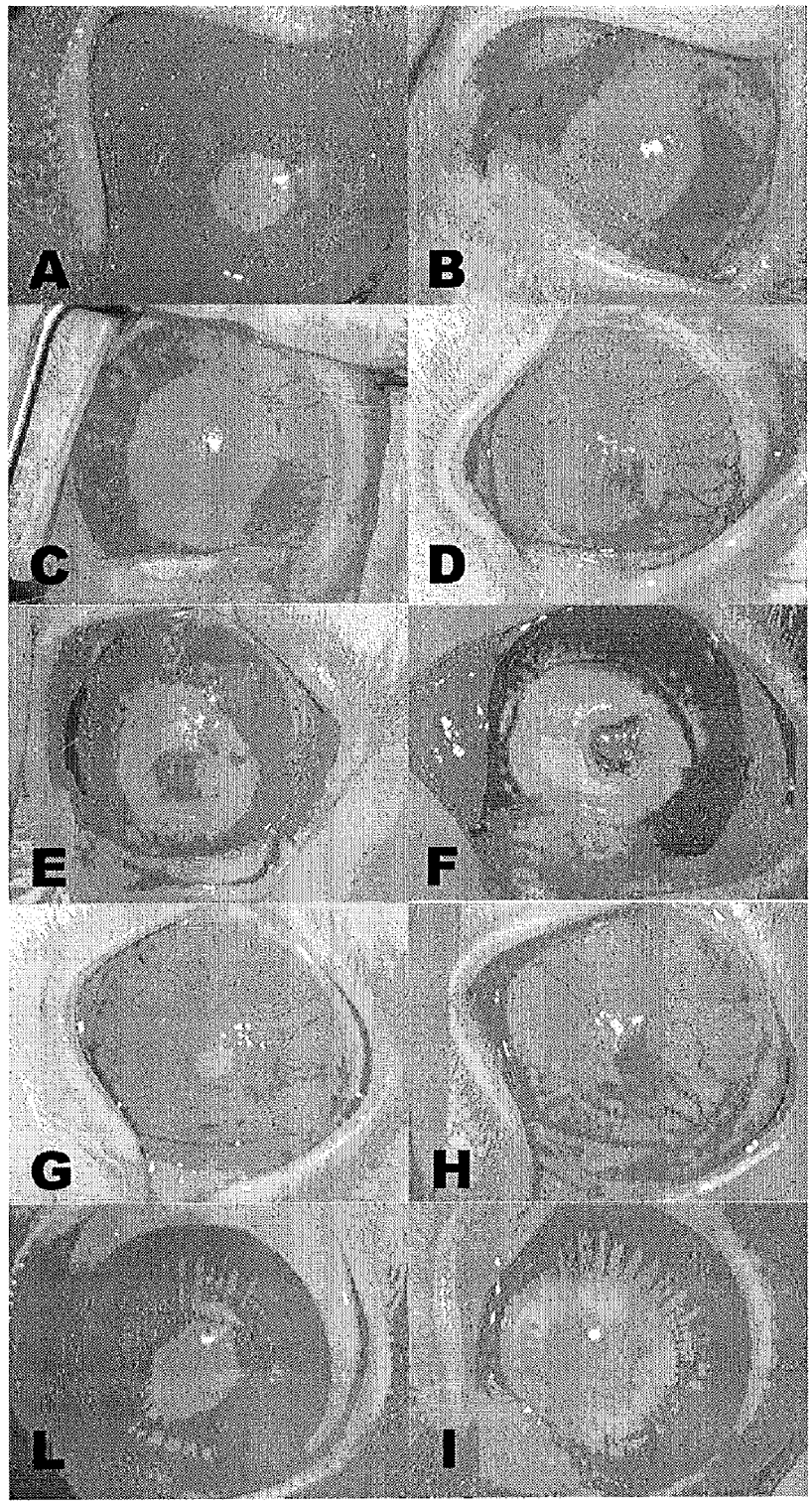
FIG. 6 is an image of a rabbit cornea, into which a porcine cornea has been lamellar-grafted. The fresh porcine corneas (control group) maintained transparency until 2 weeks post-operation (A), but showed rejection responses at 4 weeks post-operation (B). The frozen porcine corneas (freezing group) also showed rejection responses at one month post-operation (C), and the hyperosmolar glycerol-treated corneas (hyperosmolar glycerol group) became inflamed and opaque relatively earlier (D). The trypsin/Dispase/SDS group and DNase/RNase group were fused after graft (respectively, E, F). (G) and (H) show porcine corneas of 3-times freezing-thawing group at postgraft one month (G) and at two months postgrafting (H), respectively. Meanwhile, the corneas of the hypertonic saline group maintained transparency even after two months (L) and six months (I)

The survival period and corneal images of the grafts for each group are shown in Table 2 below and FIG. 6, respectively.

TABLE 2

| Groups | No | Survival period (day) |
|---|---|---|
| Control group | 7 | 20, 20, 28, 28, 30, 30, 34 |
| Freezing group | 7 | 20, 20, 20, 24, 24, 28, 28 |
| Three-times freezing-thawing group | 7 | 43, 43, 47, 47, 60, 60, 60 |
| Hypertonic saline (NaCl) group | 7 | >30, >60, >180, >180, >180, >180, >180 |
| Hyperosmolar glycerol group | 7 | 16, 18, 18, 18, 20, 20, 20 |
| Trypsin/Dispase/SDS group | 7 | 0, 0, 0, 0, 0, 0, 0 |
| Dnase/RNase group | 7 | 0, 0, 0, 0, 0, 0, 0 |

2. Histological Observation of Corneal Xenograft

At 1, 2 and 6 months post-operation, rabbits from each group were sacrificed and the corneas were extracted therefrom.

The corneal fragments were stained with H&E staining or immunofluorescence staining. The immunofluorescence staining was performed on the corneas in the presence of $CD3^+$ cells. The resulting corneas were fixed in 10% neutral buffer formalin and incubated at 4° C. overnight. The corneas were cut to 5 μm-thick, dried at 60° C. for 2 hours, and deparaffinized in xylene. Then, the resulting corneal fractions were sequentially treated with Proteinase K (20 μg/ml, Sigma, St. Louis, Mo., USA), 5% $H_2O_2$ and 0.3% triton X-100, and were supplemented with 1% serum. Monoclonal antibody against rabbit $CD3^+$ was used as a primary antibody, and PBS was used as a negative control. FITC-conjugated goat anti-rabbit IgGs (1:1000, Southernbiotech, Birmingham, Ala., USA) was used as a secondary antibody, and counterstaining was performed with Hoechst 33342 (Sigma). Then, the stained $CD3^+$ cells were observed with a fluorescence microscope.

Figure 7:
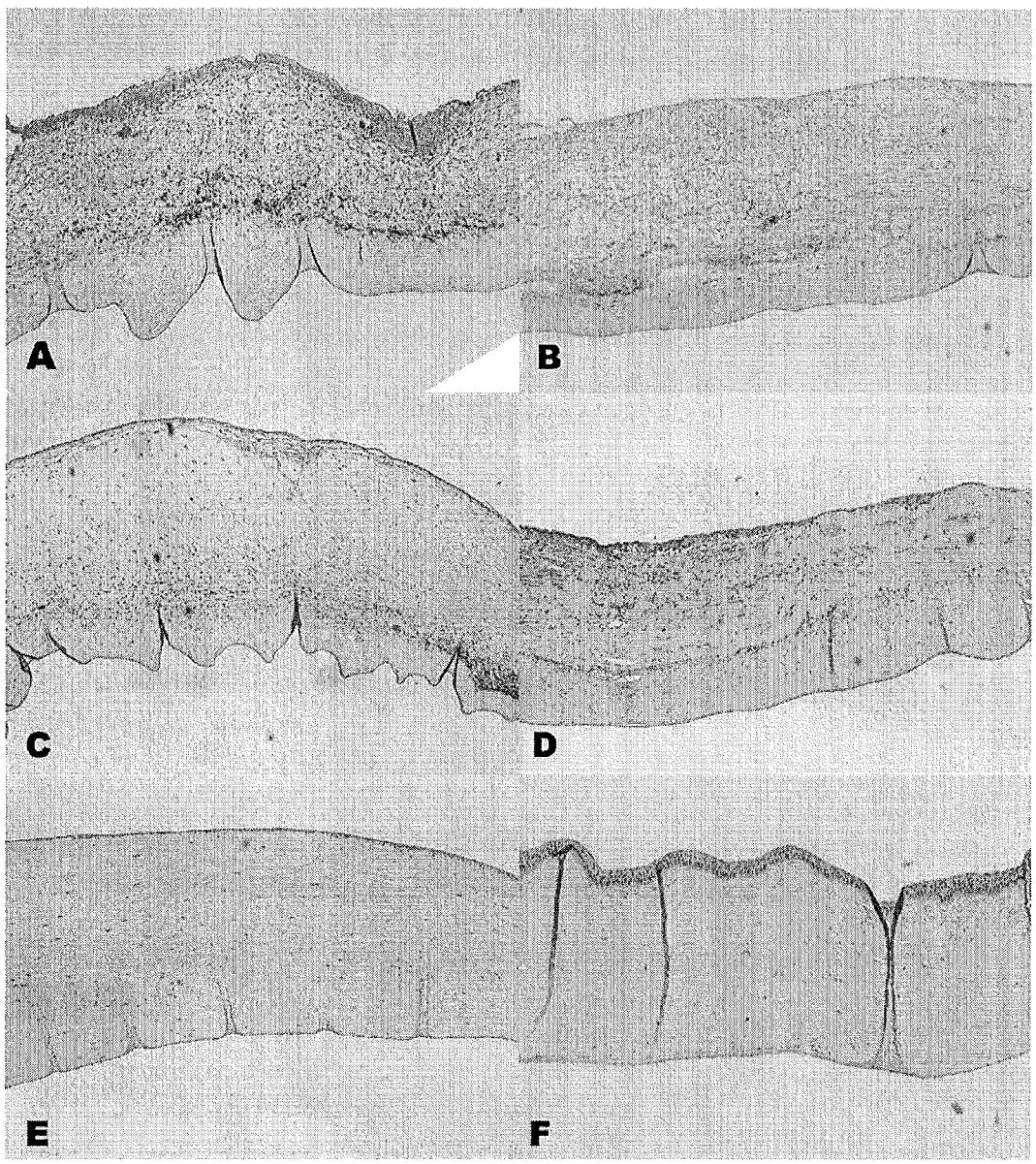
FIG. 7 shows hematoxylin-eosin staining results at one month after porcine-to-rabbit lamellar grafting. The control group had severe infiltration of inflamed cells into the donor-graft junction (A). Many inflamed cells were also observed at the freezing group (B), 3-times freezing-thawing group (C), and hyperosmolar glycerol group (D). On the other hand, the grafts of the hypertonic saline group had no inflamed cells, and were recellularized during one month postgrafting (E) and six months postgrafting (F)

Observation results ascertained that, similar to clinical examination, the H&E staining showed rejection response and severe infiltration of inflamed cells. Groups except the hypertonic saline group showed endogenous corneal neovascularization in donor-graft junction and grown into the grafts (FIG. 7). However, porcine corneas of the hypertonic saline group had no inflammation and neovascularization during postoperative 6 months.

Figure 8:
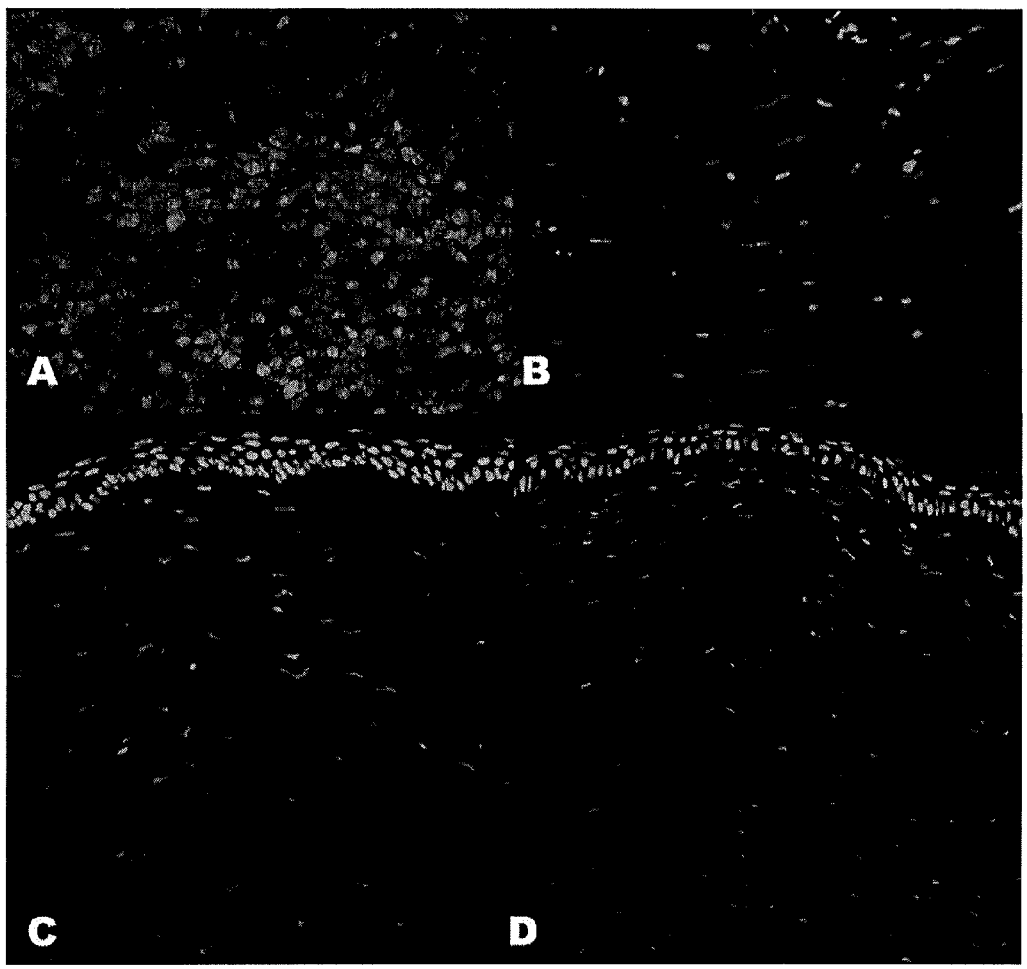
FIG. 8 shows $CD3^+$ and Hoechst 33342 immunohistochemistry staining. Many $CD3^+$ cells were observed at the grafts of the control group which showed rejection responses one month post-operation (A), whereas porcine cornea grafts of the hypertonic saline group had no $CD3^+$ cell (B). Hoechst 33342-stained keratocytes were observed throughout the hypertonic saline-treated grafts at one month post-operation (D). In this case, the number of the keratocytes was comparable to that of the normal rabbit corneal stroma.

Meanwhile, upon immunohistochemistry staining, porcine corneal grafts of the hypertonic saline group had no $CD3^+$ positive cells, while porcine corneal grafts of the control group had many $CD3^+$ positive lymphocytes (FIG. 8). Furthermore, one month after staining with Hoechst 33342 and transplantation into rabbits, decellularized porcine corneal grafts of the hypertonic saline group were reproliferated. This represents graft re-proliferation for the host keratocytes (FIG. 8).

3. In Vivo Fragment Image Research, Measurement of Corneal Thickness and Histological Findings of Corneal Xenograft The cross-sectional anterior and posterior images of full-thickness corneas were obtained monthly with anterior optical coherence tomography (OCT; Visante™ OCT Model 1000, Carl Zeiss Meditec Inc., Dublin, Calif., USA).

Figure 9:
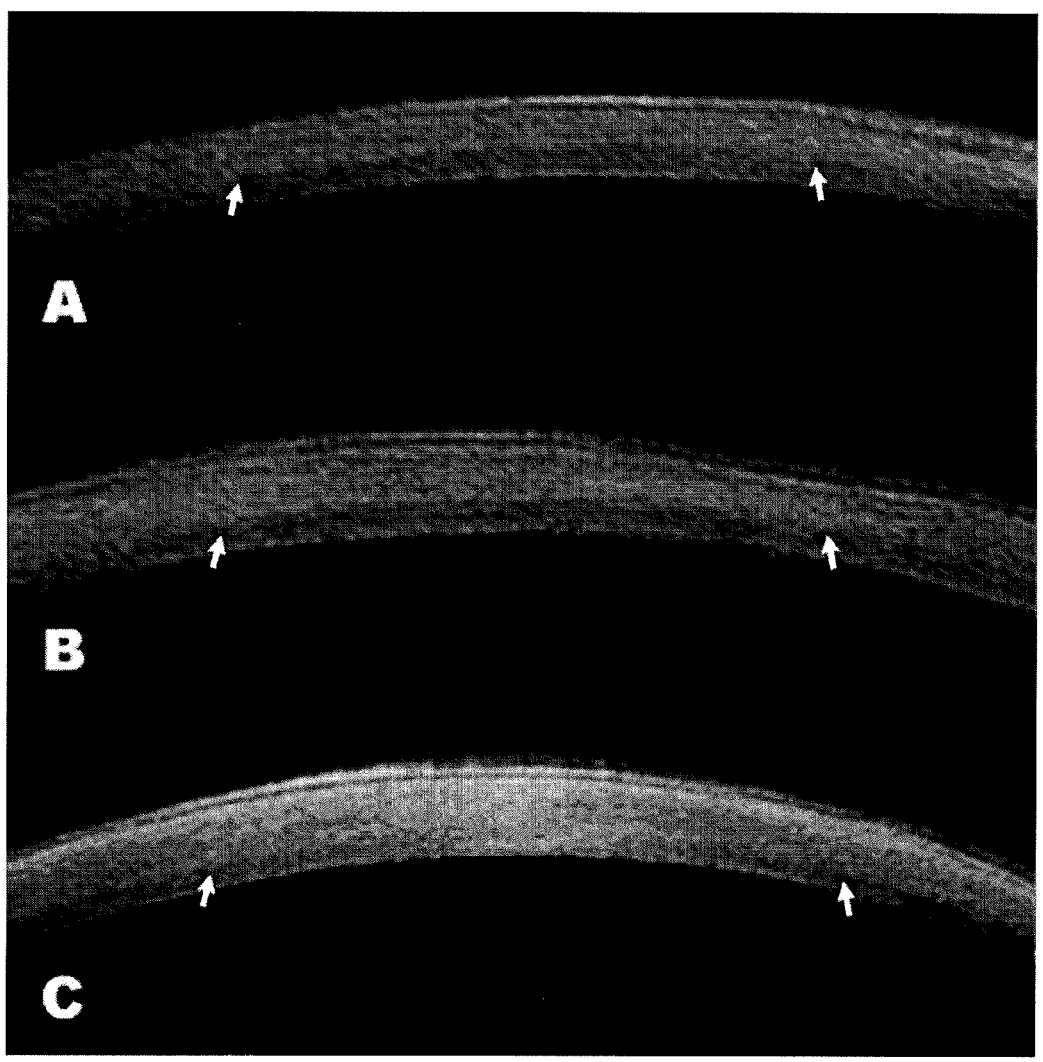
FIG. 9 is images of in vivo fragments of the rabbit cornea, into which hypertonic saline-treated porcine cornea have been grafted, at 1 month (A), 3 months (B) and six months (C) post-operation. Graft-host junctions were observed (arrow), which means that porcine grafts were suitably engrafted into the recipient corneas. At six months post-grafting, the grafted cornea was completely engrafted into the base cornea and junctions were not readily seen.

As a result of tomography, tissue fragments, in which porcine corneas were transplanted into rabbit corneas, were completely incorporated into grafts for the hypertonic saline group and successfully reconstituted into the rabbit corneas (FIG. 9).

Meanwhile, for measurement of the corneal thickness, total corneal thickness and the grafted corneal stroma thickness were measured in vivo using anterior OCT. The corneal thickness was calculated by measuring the distance between corneal epithelium and corneal endothelium, and the distance between corneal endothelium and grafted site. The total corneal thickness was measured using an ultrasonic thickness gauge (Pachymeter, Quantel Medical, Clermont-Ferrand, France).

Figure 10:
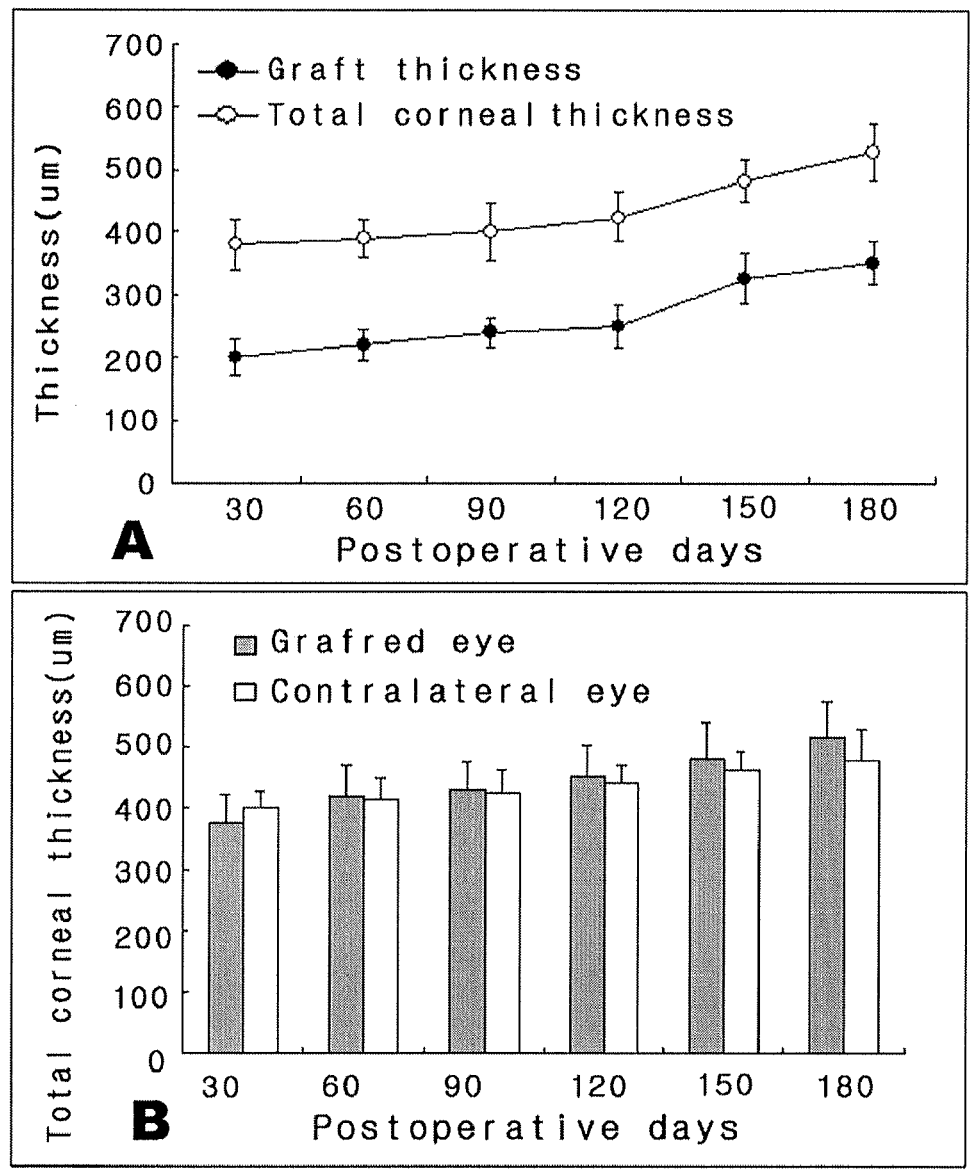
FIG. 10 is a graph comparing total corneal thickness and graft thickness of the grafted cornea (A), and a graph comparing total corneal thickness between the grafted cornea and the contralateral cornea of non-grafted eyeball (B).

As a result of the sequential measurement of corneal thickness, the thickness of the grafted porcine cornea lamellae was shown to increase, as the total corneal thickness increases, (FIG. 10A). In addition, the grafted rabbit cornea grew normally, just like the contralateral non-grafted eye.

As apparent from the above description, the present invention provides a method for processing the porcine cornea which causes neither inflammation nor immune response. The porcine corneal stroma decellularized by the method can be recellularized together with keratocytes after grafting. Accordingly, the decellularized porcine corneal stroma is useful for corneal replacements prepared by in vitro culturing and tissue engineering human corneal cells.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for processing porcine cornea, comprising the steps of:
   immersing enucleated porcine cornea in an aqueous NaCl solution, then
   immersing the porcine cornea in an aqueous trypsin/EDTA solution, and then
   washing the porcine cornea;
   wherein the aqueous NaCl solution contains 1.0 to 2.0 M NaCl.

2. The method according to claim 1, wherein the step of immersing the porcine cornea in an aqueous NaCl solution is carried out at a temperature of 35 to 39° C. for 12 to 36 hours.

3. The method of claim 2, wherein the step of immersing the porcine cornea in an aqueous trypsin/EDTA solution is carried out at a temperature of 37° C.

4. The method according to claim 1, wherein the aqueous trypsin/EDTA solution contains 0.01 to 0.10% (w/v) trypsin and 0.01 to 0.05% (w/v) EDTA.

5. The method of claim 4, wherein the step of immersing the porcine cornea in an aqueous trypsin/EDTA solution is carried out at a temperature of 35 to 39° C. for 36 to 60 hours.

6. The method of claim 5, wherein the step of immersing the porcine cornea in an aqueous trypsin/EDTA solution is carried out at a temperature of 37° C.

7. The method according to claim 4, wherein the aqueous trypsin/EDTA solution contains 0.05% (w/v) trypsin and 0.02% (w/v) EDTA.

8. The method according to claim 1, wherein the step of washing the porcine cornea is carried out using phosphate buffered solution (PBS) as a washing solution.

9. The method according to claim 1, wherein the aqueous NaCl solution contains 1.5 M NaCl.

10. The method according to claim 1, wherein the aqueous NaCl solution contains 1.5 M NaCl; and wherein the aqueous trypsin/EDTA solution contains 0.05% (w/v) trypsin and 0.02% (w/v) EDTA.

11. The method according to claim 1, wherein the aqueous NaCl solution contains 1.5 M NaCl;
   wherein the aqueous trypsin/EDTA solution contains 0.05% (w/v) trypsin and 0.02% (w/v) EDTA; and
   wherein the step of immersing the porcine cornea in an aqueous trypsin/EDTA solution is carried out at a temperature of 37° C.

* * * * *